US008494785B1

(12) United States Patent
Icenhour et al.

(10) Patent No.: US 8,494,785 B1
(45) Date of Patent: Jul. 23, 2013

(54) MOLECULAR STANDARDS FOR MICROBIAL PATHOGENS

(75) Inventors: Crystal R. Icenhour, Charlottesville, VA (US); Brian V. Loyal, Charlottesville, VA (US); Tyler Hartley, Charlottesville, VA (US); Linh Nguyen, Charlottesville, VA (US)

(73) Assignee: Phthisis Diagnostics LLC, Charlottesville, VA (US)

( * ) Notice: Subject to any disclaimer, the term of this patent is extended or adjusted under 35 U.S.C. 154(b) by 30 days.

(21) Appl. No.: 12/870,481

(22) Filed: Aug. 27, 2010

Related U.S. Application Data

(60) Provisional application No. 61/237,933, filed on Aug. 28, 2009.

(51) Int. Cl.
*G06F 19/00* (2011.01)
*C12Q 1/68* (2006.01)

(52) U.S. Cl.
USPC .............................................. 702/20; 435/6.1

(58) Field of Classification Search
None
See application file for complete search history.

(56) References Cited

PUBLICATIONS

Marck et al. (RNA (2002), 8:1189-1232).*
Krishnamachari et al. (Journal of Theoretical Biology, vol. 227, pp. 429-436, 2004).*

* cited by examiner

*Primary Examiner* — John S Brusca
(74) *Attorney, Agent, or Firm* — Baker & Hostetler LLP

(57) ABSTRACT

A method for constructing a consensus sequence from a sequence alignment. The consensus sequence may be used to generate molecular standards that may substitute for genomic DNA in various assays. Since a molecular standard cannot have unresolved bases, the method removes less informative sequences to resolve all positions in the alignment. Also includes several sequences from pathogenic waterborne species that were constructed according to the method.

10 Claims, 6 Drawing Sheets

MOLECULAR STANDARDS FOR MICROBIAL PATHOGENS

CROSS-REFERENCE TO RELATED APPLICATIONS

This application claims priority under 35 U.S.C. §119(e) to provisional U.S. Patent Application No. 61/237,933, filed on Aug. 28, 2009, the disclosure of which is expressly incorporated by reference herein in its entirety.

STATEMENT OF GOVERNMENT INTEREST

The United States Government may own rights in the present disclosure pursuant to NIH 2 R42 A1069598-02 and NSF 0945221.

BACKGROUND

1. Field of the Present Disclosure

The present disclosure provides a library of synthetic standard molecules for multiple species of microbial pathogens, including *Cryptosporidium, Giardia*, and microsporidia. Each of these standard molecules includes a bacterial plasmid molecule containing a specific DNA sequence insert that represents a consensus sequence of the 18s rRNA gene for a single species of interest. These standard molecules may be used by, for example, researchers, utility operators, and clinical laboratory technicians as a surrogate for native genomic DNA in a variety of situations.

2. Related Art

Due to technological limitations, environmental and clinical laboratories are increasingly moving away from microscopic methods and towards molecular detection methods. Molecular methods typically use the polymerase chain reaction (PCR) to detect a specific DNA sequence in the genome of a target organism. Compared to microscopic methods, molecular methods offer increased speed, sensitivity, and reproducibility. Molecular methods can also provide supplementary data unattainable using microscopy, such as, for example, genotype identification.

One microbial pathogen of particular interest is *Cryptosporidium*. Fifteen waterborne *Cryptosporidium* outbreaks were reported in the United States between 1991 and 2002, affecting over 408,000 individuals. This makes *Cryptosporidium* the highest cause of waterborne disease by number of affected individuals. The most significant outbreak occurred in Milwaukee, Wis. in 1993. This well-studied case affected over 403,000 individuals and cost the region an estimated $96.2 million. This event, plus several major recreational outbreaks since then, underscores the importance of proper water monitoring.

*Giardia* contamination can cause outbreaks that result in similar disruptions.

Microsporidia, including *Encephalitozoon intestinalis* and *Enterocytozoon bieneusi*, cause microspridiosis, which is an opportunistic infection that can cause diarrhea and wasting in immunocompromised patients.

Unfortunately, the introduction of new molecular tools for targets such as, e.g., *Cryptosporidium* and *Giardia* has been restricted by the lack of standardized positive controls. Positive controls, typically purified genomic DNA from pathogens of interest, may have multiple roles in the development and validation of a molecular method. Two of the most important roles include:

As a sensitivity control, determining detection limits and quantifying target DNA; and As a specificity control, resolving target genotypes.

It can be extremely challenging to obtain positive controls for microbial pathogens of environmental interest. Many such organisms are difficult to culture in vitro. The distribution of others is regulated by the Centers for Disease Control and/or the United States Department of Commerce. Researchers who wish to develop new tests for these pathogens must often perform their own isolations from clinical or environmental samples or obtain specimens from collaborators. These research stocks are often subject to inconsistent quality control, increase the risk of laboratory-associated infections, and are of insufficient quantity for industrial-scale development and validation. Until an alternative source can be developed, the limited availability of positive controls threatens to prevent the introduction of any new molecular tests for microbial pathogens into the market.

In the case of *Cryptosporidium*, limited amounts of positive control DNA are available from a handful of Biological Resource Centers (BRCs). In particular, Waterborne supplies purified *C. parvum* and *C. muris* oocysts, while AMERICAN TYPE CULTURE COLLECTION™ (ATCC) can regularly provide researchers with genomic DNA from *C. parvum* (Iowa strain). A third commercial source, the Biodefense and Emerging Infections Research Resources Repository (BEI Resources), supplies genomic DNA and other reagents only to NIH-funded investigators. These supplies are insufficient for widespread method development, especially for assays aimed at distinguishing multiple genotypes. As a result, test development has been fragmented as research groups rely on various organism stocks of inconsistent quality.

Accordingly, there exists a pressing need for standardized positive controls for *Cryptosporidium, Giardia*, microsporidia, and other microbial pathogens that may be used to develop and validate moleculr detection and genotyping methods.

SUMMARY OF THE PRESENT DISCLOSURE

The present disclosure meets the foregoing need and allows detection of pathogenic species using molecular methods, which results in a significant improvement in speed, sensitivity, and reproducibility and other advantages apparent from the discussion herein.

Accordingly, in one aspect of the present disclosure, a method is described for constructing a consensus sequence from an alignment of two or more nucleic acid sequences. The method includes iterating over each position in the alignment and taking the following actions at each position: (1) calculate the base frequencies and determine the base with the highest frequency; (2) if the frequency of the most common base with the highest frequency is greater than a specified frequency threshold, then the base is assigned to that position in the consensus sequence; and (3) if the frequency of the most common base is below the frequency threshold, then the base corresponding to the nucleic acid sequence with the lowest information score is removed and the process repeats from action (1).

The method may include generating a frequency matrix, which includes the frequency of each base at each position in the alignment; creating an information matrix, which includes the amount of information provided by each base at each position in the alignment; and calculating an information score for each nucleic acid sequence. As part of creating an information matrix, the method may calculate the decrease in Shannon uncertainty for each base at each position in the alignment. As part of calculating an information score, the method may sum the decreases in Shannon uncertainty for each base in each sequence. Insertions and Deletions may be removed from the multiple sequence alignment. The frequency threshold for actions (2) and (3) may be 0.7.

The method may be used to construct a consensus sequence. A restriction fragment length polymorphism (RFLP) fingerprint of the constructed consensus sequence may be compared to RFLP fingerprints of one or more of the nucleic acid sequences in the multiple sequence alignment. Binding of oligonucleotides to the consensus sequence and to sequences in the multiple sequence alignment may be compared on the basis of Gibb's free energy of hybridization, melting temperature of the heterodimer, and binding position. The consensus sequence may be used to synthesize a DNA construct or molecular standard. The DNA construct may be linear, or it may be circular, e.g., a plasmid.

According to another aspect of the present disclosure, a multiple sequence alignment, which includes a number of alignment positions, is used to construct a consensus sequence. As part of this method, a frequency matrix, which includes the frequency of each base at each alignment position, is generated. An information matrix, which includes the amount of information provided by each base at each alignment position, is also generated, and an information score is calculated for each sequence in the multiple sequence alignment. The method iterates over the alignment and at each alignment position, does the following: (1) determining which base at the alignment position has the highest frequency; (2) if the frequency of the highest frequency base is above a threshold value, the base is assigned to the consensus sequence; and (3) if the frequency of the highest frequency base is below the threshold, the base corresponding to the sequence with the lowest information score is removed, base frequencies are recalculated, and the procedure returns to action (1).

As part of creating an information matrix, the method may calculate the decrease in Shannon uncertainty for each base at each position in the alignment. As part of calculating an information score, the method may sum the decreases in Shannon uncertainty for each base in each sequence. Insertions and Deletions may be removed from the multiple sequence alignment. The frequency threshold for actions (2) and (3) may be 0.7.

The method may be used to construct a consensus sequence. A restriction fragment length polymorphism (RFLP) fingerprint of the constructed consensus sequence may be compared to RFLP fingerprints of one or more of the nucleic acid sequences in the multiple sequence alignment. Binding of oligonucleotides to the consensus sequence and to sequences in the multiple sequence alignment may be compared on the basis of Gibb's free energy of hybridization, melting temperature of the heterodimer, and binding position. The consensus sequence may be used to synthesize a DNA construct or molecular standard. The DNA construct may be linear, or it may be circular, e.g., a plasmid.

According to yet another aspect of the present disclosure, 18S rRNA consensus sequences are disclosed for *Cryptosporidium andersoni*, as shown in SEQ ID NO:1; *Cryptosporidium baileyi*, as shown in SEQ ID NO:2; *Cryptosporidium bovis*, as shown in SEQ ID NO:3; *Cryptosporidium canis*, as shown in SEQ ID NO:4; *Cryptosporidium felis*, as shown in SEQ ID NO:5; *Cryptosporidium hominis*, as shown in SEQ ID NO:6; *Cryptosporidium meleagridis*, as shown in SEQ ID NO:7; *Cryptosporidium muris*, as shown in SEQ ID NO:8; *Cryptosporidium parvum*, as shown in SEQ ID NO:9; *Cryptosporidium serpentis*, as shown in SEQ ID NO:10; *Cryptosporidium wrairi*, as shown in SEQ ID NO:11; *Giardia intestinalis*, as shown in SEQ ID NO:12; *Encephalitozoon intestinalis*, as shown in SEQ ID NO:13; and *Enterocytozoon bieneusi*, as shown in SEQ ID NO:14.

Additional features, advantages, and embodiments of the present disclosure may be set forth or apparent from consideration of the following detailed description, drawings, and claims. Moreover, it is to be understood that both the foregoing summary of the present disclosure and the following detailed description are exemplary and intended to provide further explanation without limiting the scope of the present disclosure as claimed.

BRIEF DESCRIPTION OF THE DRAWINGS

The accompanying drawings, which are included to provide a further understanding of the present disclosure, are incorporated in and constitute a part of this specification, illustrate embodiments of the present disclosure and together with the detailed description serve to explain the principles of the present disclosure. No attempt is made to show structural details of the present disclosure in more detail than may be necessary for a fundamental understanding of the present disclosure and the various ways in which it may be practiced. In the drawings.

DETAILED DESCRIPTION

Figure 1:
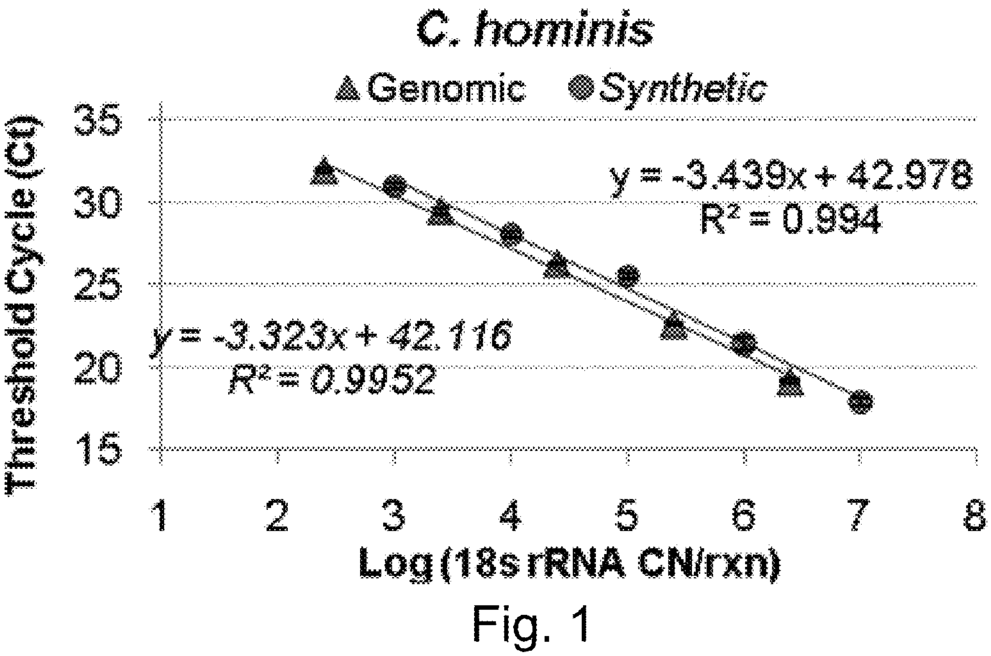
FIG. 1 shows standard curves of *C. hominis* genomic and synthetic target DNA in real-time PCR assays.

It is understood that the present disclosure is not limited to the particular methodology, protocols, and reagents, etc., described herein, as these may vary as the skilled artisan will recognize. It is also to be understood that the terminology used herein is used for the purpose of describing particular embodiments only, and is not intended to limit the scope of the present disclosure. It also is be noted that as used herein and in the appended claims, the singular forms "a," "an," and "the" include the plural reference unless the context clearly dictates otherwise. Thus, for example, a reference to "a capsule" is a reference to one or more capsules and equivalents thereof known to those skilled in the art.

Unless defined otherwise, all technical and scientific terms used herein have the same meanings as commonly understood by one of ordinary skill in the art to which the present disclosure pertains. The embodiments of the present disclosure and the various features and advantageous details thereof are explained more fully with reference to the non-limiting embodiments and/or illustrated in the accompanying drawings and detailed in the following description. It should be noted that the features illustrated in the drawings are not necessarily drawn to scale, and features of one embodiment may be employed with other embodiments as the skilled artisan would recognize, even if not explicitly stated herein.

Any numerical values recited herein include all values from the lower value to the upper value in increments of one unit provided that there is a separation of at least two units between any lower value and any higher value. As an example, if it is stated that the concentration of a component or value of a process variable such as, for example, size, temperature, pressure, time and the like, is, for example, from 1 to 90, specifically from 20 to 80, more specifically from 30 to 70, it is intended that values such as 15 to 85, 22 to 68, 43 to 51, 30 to 32 etc., are expressly enumerated in this specification. For values which are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

Moreover, provided immediately below is a "Definition" section, where certain terms related to the present disclosure are defined specifically. Particular methods, devices, and materials are described, although any methods and materials similar or equivalent to those described herein can be used in the practice or testing of the present disclosure. All references referred to herein are incorporated by reference herein in their entirety.

1. DEFINITIONS

The terms "alignment" and "sequence alignment" as used herein refer to arrangement of two or more nucleic acid sequences that may be used to identify regions of similarity between the sequences. If the sequences are displayed horizontally, then the individual bases from different sequences are arranged in vertical columns, which may be referred to as "alignment positions".

The term "base" as used herein refers to a single monomer of a nucleic acid.

The term "base frequency" as used herein refers to the frequency with which a given base appears in a particular grouping of bases, such as a nucleic acid sequence or an alignment position.

The term "consensus sequence" as used herein refers to a representation of a sequence alignment that The term "*Cryptosporidium*" as used herein by itself, not followed by a species name, means any species of *Cryptosporidium* which is known to cause disease, including, for example, *C. parvum, C. felis, C. muris, C. meleagridis, C. suis, C. canis*, and/or *C. hominis*.

The term "DNA construct" as used herein refers to an artificially constructed segment of nucleic acid.

The term "*Giardia*" as used herein by itself, not followed by a species name, means any species of *Giardia* which is known to cause disease. This may include, for example, *G. lamblia, G. duodenalis*, and/or *G. intestinalis*.

The term "microsporidia" as used herein refers to any species of microsporidia which is known to cause disease, including, e.g., *E. intestinalis* and/or *E. bieneusi*.

The term "nucleic acid," as used herein, may include an oligonucleotide, nucleotide, or polynucleotide, and fragments thereof. The term may refer to DNA or RNA of genomic or synthetic origin, which may be single- or double-stranded and may represent the sense or antisense strand. Additionally, the term may refer to peptide nucleic acid (PNA), to small interfering RNA (siRNA) molecule, or to any DNA-like or RNA-like material, natural or synthetic in origin.

The term "nucleic acid sequence" as used herein refers to the specific order of monomers in a nucleic acid molecule that includes two or more monomers.

The term "PCR" as used herein means the polymerase chain reaction, as is well-known in the art. The term includes all forms of PCR, such as, e.g., real-time PCR and quantitative PCR.

The term "plasmid" as used herein refers to a circular nucleic acid molecule that is separate from a cell's chromosome(s) and may replicate independently of the chromosome(s).

The terms "restriction fragment length polymorphism" and "RFLP" as used herein refer to a difference between two or more nucleic acid samples. Differences in sequence between the samples result in different endonuclease restriction (cutting) sites, which in turn produce fragments of different length after digestion by a particular endonuclease. The particular pattern of fragments that a sample produces may be referred to as a "RFLP fingerprint."

2. DESCRIPTION

Molecular methods are increasingly used for the detection of pathogens, due to superiority of these methods over traditional microscopic methods. Molecular tools for many pathogenic species, however, may be unavailable because the organisms are difficult to culture in vitro, resulting in a lack of standardized positive controls. Consequently, researchers often rely on their own isolations, which can vary dramatically in quality. Development of molecular methods is fragmented as different groups rely on organism stocks of inconsistent quality. Thus, there is need for standardized positive controls for these organisms, such as, e.g., *Cryptosporidium, Giardia*, and microsporidia, that can be used to develop and validate molecular detection and genotyping methods.

One promising solution may be found in the advancing field of synthetic biology. Synthetic biology involves using engineering tools to generate biological components de novo from DNA sequences. Much of this work relies on recent improvements in chemical DNA synthesis by third-party manufacturers.

One aspect of the present disclosure is directed to a robust workflow for designing synthetic positive controls. This workflow has been employed to produce consensus sequences for *Cryptosporidium hominis, C. meleagridis, C. felis, C. parvum, C. muris, C. andersoni, C. baileyi, C. bovis, C. canis, C. serpentis, C. wrairi, Giardia intestinalis, Encephalitozoon intestinalis*, and *Enterocytozoon bieneusi*. Additionally, molecular standards have been produced and tested for C. felis, C. parvum, C. muris, C. hominis, C. meleagridis, and G. intestinalis. Each of these molecular standards may include a bacterial plasmid molecule containing a synthetically-produced DNA insert, the sequence of which may represent the 18s rRNA gene of a single *Cryptosporidium, Giardia*, or microsporidia species. These molecular standards may be used as a surrogate for native genomic DNA in a variety of situations.

This approach has a number of advantages over traditional sources of positive control DNA, including, for example, the following:

- The efficiency of chemical DNA synthesis allows rapid prototyping and validation.
- Synthetic standards are extremely stable, extending storage life and ensuring high-quality analytical results.
- Synthetic standards can be designed to allow use by multiple research teams to develop and validate their molecular assays.
- The design and production of synthetic standards can be subjected to precise quality control.
- Synthetic standards present a lower risk of laboratory contamination than live organism cultures, allowing easier distribution and use by academic, commercial, and educational groups.

The design workflow described in this disclosure includes six parts, including:

1. Identify relevant reference sequences for the target gene.
2. Align the reference sequences using one of several existing software applications.
3. Reduce the multiple sequence alignment into a single consensus sequence using a novel algorithm.
4. Computationally verify that the consensus sequence exhibits the same properties as one or more reference sequences.
5. Synthesize the consensus sequence and incorporate it into a bacterial plasmid to create a molecular standard.
6. Optimize PCR performance of the molecular standard.

Each of these parts will now be described in detail.

Part 1: Identify Relevant Reference Sequences.

For most pathogens of interest, there is a general consensus in the scientific literature as to which gene represents the most appropriate target for molecular assays. In the case of *Cryptosporidium, Giardia*, and microsporidia, this gene is 18s rRNA. However, alternative genes may be used in these or other species without departing from the spirit or scope of the present disclosure. The selected gene or genes may or may not include additional flanking sequences. The first step in the design workflow is to collect as many 18s rRNA reference sequences for the species of interest as possible. Many of these are available on public databases, such as, for example, GENBANK™. However, other sequences may be obtained as part of a private sequencing effort.

Some reference sequences may be more valuable than others. For example, sequences that were obtained many years ago may reflect incorrect naming conventions or include inaccurate information. These distinctions should be made to ensure that only the most accurate reference sequences are used to design the molecular standards. Ideally, at the end of Part 1, a list of reference sequences should have been determined. The list should represent the efforts of multiple sequencing groups, at different geographic locations, analyzing multiple strains or isolates.

Part 2: Align Reference Sequenced Using One of Several Multiple Sequence Alignment Applications.

In order for the reference sequences to be useful, they should first be aligned to each other. Although each sequence may be from the same species, they all will likely be from different isolates or sub-species. Each of these sub-species may have subtle differences in the sequence of their 18s rRNA gene. Also, due to variability in sequencing equipment and protocols, each reference sequence may likely be of a unique length. Long sequences may be likely to contain many different patterns, while smaller sequences may be likely to contain only a subset of these patterns. By aligning these sequences, it is possible to identify regions of similarity between some or all of the sequences.

For example, an unaligned set of four sequences may be represented as:

ACTGGTAGCTAGCCTGGATCGATCGGGT-GTAGTACTGA SEQ ID NO: 15
TAGCCTGGATCCATCG SEQ ID NO: 16
TATTACTGA SEQ ID NO: 17
TAGGTAGCCTGGATC SEQ ID NO: 18

The alignment of these four sequences may be represented as:

ACTGGTAGCTAGCCTGGATCGATCGGGT-GTAGTACTGA SEQ ID NO: 19
---------TAGCCTGGATCCATCG------------- SEQ ID NO: 20
---------------------------TATTACTGA SEQ ID NO: 21
-----TAGGTAGCCTGGATC----------------- SEQ ID NO: 22

Many third-party software applications exist to perform multiple sequence alignments, including, for example, MUSCLE, MAFFT, MACAW, T-Coffee, and CLUSTAL. Alignments used in the development of the present disclosure were obtained using CLUSTAL. The output of CLUSTAL included a text file containing a multiple sequence alignment of all reference sequences identified during Part 1.

Part 3: Reduce the Multiple Sequence Alignment to a Single Consensus Sequence.

The multiple sequence alignment obtained during Part 2 may represent all of the various sequences a researcher might obtain if he or she sequenced the 18s rRNA gene of the *Cryptosporidium, Giardia*, or microsporidia species of interest from a particular source. However, it may not be possible to determine which of the reference sequences may be the most representative of the researcher's particular isolate. Therefore, it may not be possible to simply select an arbitrary reference sequence and use it as the basis for a molecular standard because the arbitrarily selected sequence may not bear enough similarities to the researcher's isolate.

Instead, a single consensus sequence may be generated from the multiple sequence alignment. This consensus sequence may not be identical to any of the reference sequences. However, it may be closely similar to all of them. In this way, it may be possible to ensure that the molecular standard may be useable by all researchers working with the species of interest, regardless of their particular isolate.

The consensus sequence determination may be made using a multi-part computational algorithm:

Part 3a: Remove Base Pair Inserts and Deletions.

During the alignment of the DNA sequences as outlined in Part 2, the alignment software may discover an insert (an unnecessary base) or a deletion (a missing base) in one or more sequences. These inserts and deletions should be removed before further analysis. For example, consider a sequence alignments represented as:

TATCAACAT_CCTTCCTATTATATTTCT SEQ ID NO: 23
TATCAACAT_CCTTCCTATTATAT_TCT SEQ ID NO: 24
TATCAACATTCCTTCCTATTATATTTCT SEQ ID NO: 25
TATCGACAT_CCTTCCTATTATATATCT SEQ ID NO: 26

At position 10 of the example alignment, sequence 3 has a base insert that does not exist in any other sequence. In a method according to the present disclosure, this inserted base may be removed. Sequence 2 has a deletion that occurs at position 25. Due to the existence of a larger number of bases at that position, these bases may not be removed.

Part 3b: Create Frequency Matrix.

A frequency matrix may be generated, containing the frequency of each base at each alignment position. For example, consider 5 reference sequences aligned in the following way:

| Position # | 1 | 2 | 3 |
|---|---|---|---|
| Sequence 1 | A | C | T |
| Sequence 2 | A | C | A |
| Sequence 3 | T | G | C |
| Sequence 4 | A | G | C |
| Sequence 5 | A | T | G |

In this case, the frequency matrix would be:

| Position # | 1 | 2 | 3 |
|---|---|---|---|
| f(A): | 0.8 | 0 | 0.2 |
| f(T): | 0.2 | 0.2 | 0.2 |

-continued

| Position # | 1 | 2 | 3 |
|---|---|---|---|
| f(C): | 0 | 0.4 | 0.4 |
| f(G): | 0 | 0.4 | 0.2 |

where f(A) is the frequency of Adenine (A) at that alignment position, f(T) the frequency of Thymine (T), etc.

Part 3c: Create Information Matrix.

Using the frequency matrix, an information matrix may be created containing the amount of "information" provided by a given base i at each alignment position j. In this case, information may be defined as the decrease in Shannon uncertainty, calculated as:

$$I_{i,j}=2+\log_2(p_{i,j})$$

where is the frequency of base i at alignment position j.

In the instant example, the following information matrix may be obtained:

| Position # | 1 | 2 | 3 |
|---|---|---|---|
| f(A): | 0.8 | 0 | 0.2 |
| f(T): | 0.2 | 0.2 | 0.2 |
| f(C): | 0 | 0.4 | 0.4 |
| f(G): | 0 | 0.4 | 0.2 |

| Position # | 1 | 2 | 3 |
|---|---|---|---|
| I(A): | 1.68 | ∞ | −0.32 |
| I(T): | −0.32 | −0.32 | −0.32 |
| I(C): | ∞ | 0.68 | 0.68 |
| I(G): | ∞ | 0.68 | −0.32 |

Part 3d: Determine an Information Score for Each Reference Sequence

The information matrix determined in Part 3c describes the amount of information provided by a given nucleotide at each alignment position. By summing these information contributions along the entire length of a given sequence, an information score may be determined. This score may represent the total amount of information encoded into the sequence. Sequences with high scores may contain many bases that are shared with other aligned sequences at that position. Sequences with low scores may be regarded as "unusual", containing low-frequency bases at many alignment positions.

In the instant example, Sequence 1 may be scored in the following fashion:

| Sequence 1 | A | C | T |
|---|---|---|---|
| $I_A$: | 1.68 | ∞ | −0.32 |
| $I_T$: | −0.32 | 0.32 | −0.32 |
| $I_C$: | ∞ | 0.68 | 0.68 |
| $I_G$: | ∞ | 0.68 | −0.32 |

Thus, $I_{sequence\ 1}=1.68+0.68+(-0.32)=2.04$ bits of information

Since the aligned sequences may be of different lengths, the information content of each sequence may be normalized by the number of by it contains:

$$T_{sequence\ 1}=2.04/3=0.68 \text{ bits/bp}$$

By applying this logic to the entire multiple sequence alignment, it may be possible to determine which of the reference sequences are most relevant to the consensus sequence.

The concept of sequence information has been used by others to identify sequence motifs, specific sequences conserved across many genomes that may indicate undiscovered genes, protein-binding sites, or other biochemical or structural information.

Part 3e: Determine Consensus Sequence.

Once information scores have been generated for each reference sequence, the multiple sequence alignment may be reduced to a single consensus sequence. There are many ways to determine a consensus sequence, as known by those having ordinary skill in the relevant art. For instance, a popular way is to select the most frequent base at each position in an alignment. The literature describes a method for determining a consensus sequence where the most frequent base is selected for each position if its frequency is ≧0.875. However, if the frequency is less than that, the consensus base is left undefined for that position. Undefined bases, however, are not suitable for synthesis and incorporation into a molecular standard because there must be a base at every position in the sequence. Thus, the present disclosure uses a novel process.

To determine a consensus sequence, analysis may begin at the first alignment position and move toward the last alignment position. At each alignment position, the following decisions may be made, including:

i. Is the highest frequency of any base greater than 0.7? If yes, assign that base to the consensus sequence and move to the next position. If no, go to step ii.

ii. Look at the alignment of bases at that position. Which one comes from the reference sequence with the lowest I score? Remove it from consideration and go to step iii.

iii. After one instance of a base has been removed, recalculate the base frequencies. Go back to step i.

A method for determining a consensus sequence may use the most common base at a given position, even if that base is only slightly more common than the others, e.g. a frequency of 0.26. The cutoff frequency of 0.7 may be selected to balance the consideration given to less common bases. A lower cutoff may give such outliers too much weight while a higher cutoff may give them too little weight.

Part 4: Computationally Verify the Consensus Sequence.

Prior to synthesis, computational tools may be used to predict whether the consensus sequence will behave similarly to one or more of the reference sequences.

Part 4a: In Silico RFLP Digest.

Restriction Fragment Length Polymorphism (RFLP) analysis is a common molecular biology technique for identifying differences between multiple DNA samples. During RFLP analysis, one or more restriction endonucleases may be used to digest the DNA samples of interest. A restriction endonuclease may include an enzyme that cuts DNA at specific recognition sites. For example, the EcoRI enzyme may cut a double-stranded DNA recognition sequence in the following fashion ('|' indicates a cut point):

```
5' G|AATT C 3'

3' C TTAA|G 5'
```

After digestion, the fragments of each DNA sample may be separated by size using, for example, gel electrophoresis, producing a "fingerprint" that can be used to identify small sequence differences between the DNA samples. During in silico RFLP digest, a sequence may be computationally searched for a set of known restriction endonuclease recognition sites, and the number of bases in between the sites may be counted. With this information, a model RFLP fingerprint may be created for that sequence. Ideally, the consensus sequence and reference sequences should have the same number of RFLP fragments. Also, the corresponding fragments for each sequence should be approximately the same length. If this is not the case, the consensus sequence may need to be redesigned.

Part 4b: Primer/Probe Binding Simulation.

To determine if the consensus sequence is a good surrogate for the reference sequences, the behavior of these sequences in previously-published molecular assays may be simulated. Most molecular assays rely upon the use of short pieces of DNA referred to as oligonucleotides. Oligonucleotides may function as PCR primers, guiding the amplification of certain genetic regions. Oligonucleotides may also function as probes, binding to specific regions of the target DNA and emitting a signal of some sort. In both cases, assay performance may be dependent upon the oligonucleotides binding tightly to the target DNA in the correct location.

During computational verification, the way that the oligonucleotides described in previously-published molecular assays bind to the consensus and reference sequences may be simulated. A software tool, such as, for example, VisualOMP, may be used to perform these simulations, although other such tools exist. Ideally, each oligonucleotide should bind to the consensus and reference sequences with the same strength (indicated by the Gibb's free energy of hybridization and melting temperature of the heterodimer) and binding position. If this is not the case, the consensus sequence may need to be redesigned.

Part 5. Synthesize the Molecular Standard.

Once a consensus sequence has been identified and computationally verified, it may be synthesized and incorporated into a molecular standard. The resulting molecular standard may include a circular DNA plasmid containing the consensus sequence as an insert. Other types of constructs are contemplated and within the scope of the present disclosure. The use of a plasmid carrier molecular provides stability to the molecular standard, extending shelf life and allowing use in a variety of molecular assays. Creation of the molecular standard may be accomplished by any means known to those skilled in the art, including ordering the standard from a third party manufacturer. One such third party manufacturer is Blue Heron Biotechnology, although there are others.

Part 6. Optimize the PCR Performance of the Molecular Standard.

Even though a molecular standard may share an identical insert sequence as a sample of native genomic DNA, the two templates may not behave identically during molecular analysis. Due to the small size of each plasmid, a vial of molecular standard may contain many more copies of the insert per mass of DNA than the genomic material. Genomic material may also contain many orders more non-target DNA than the molecular standards. For these reasons, molecular standards may produce much clearer results than native genomic DNA. In the case of PCR-based assays, this means that the genomic DNA may amplify with lower efficiency. This performance bias may be unacceptable if the molecular standards are to serve as surrogates for native genomic material.

To ensure that the molecular standards demonstrate PCR efficiency similar to native genomic material, it may be necessary to introduce PCR inhibitors to the standard solutions. Many such inhibitors exist, such as, e.g., non-target DNA, humic acids, polysaccharides; bile salts, immunoglobin G, heme, CTAB, SDS, alcohol, sodium acetate, sodium chloride, EDTA, collagen, melanin, eumelanin, myoglobin, proteinases, calcium ions, urea, lactoferrin, indigo dye, and the like. By introducing one or more of these substances into solution with the molecular standards, the PCR efficiency of the standards may be optimized to match that of native genomic DNA. This process of using PCR inhibitors to adjust the amplification efficiency of the molecular standards may be a key component of guaranteeing their utility.

The process described above results in standardized positive controls for microbial pathogens that may be used to develop and validate molecular detection and genotyping methods. Historically, most efforts in this area have focused on developing PCR inhibition positive controls, also known as internal controls. These typically involve generating either a linear or plasmid DNA template containing a short (<1,000 bp) insert, usually a PCR amplicon, flanked by specific primer recognition sites. These molecules are then spiked into analytical reactions to distinguish "no target" samples (internal control will amplify) from false negatives (internal control will not amplify, typically due to matrix inhibition). This approach has been used in assays for various organisms, including HSV 1 and 2, avian influenza, pestiviruses, *Agrobacterium tumefaciens*, and others.

Due to small insert size and targeted design, traditional internal controls, such as those listed above, share the same limitation: they are necessarily assay-specific and cannot be used with alternative primer or probe sets. Therefore, research groups developing new detection or genotyping assays must also generate their own internal controls from scratch. In contrast, the molecular standards disclosed herein involve significant portions of target genes, if not the entire sequence. In this way, any test developer targeting a selected gene can use the molecular standards, regardless of their assay's specific primer or probe sequences.

Molecular standards developed according to the disclosure may be used as surrogates for native genomic DNA in a number of applications for various users. Molecular assay developers may use the molecular standards to determine the suitability of PCR primers and probes during development, to determine limit-of-detection specifications during development, or to verify the species-specificity of PCR primers and probes during development. End-users of a molecular assay may use the molecular standards to generate standard curves when quantifying the amount of target in a sample during qPCR, as a positive control to determine if a particular PCR reaction mixture was created and pipetted correctly, as a spike-in control to determine the amount of PCR inhibition present in a sample matrix, as a spike-in control to determine the recovery of a particular DNA extraction technique, or as a genotype control to compare against during genotyping assays, such as RFLP.

EXPERIMENTS

The above process was used to generate consensus sequences for 11 species of *Cryptosporidium* (*C. felis, C. parvum, C. muris, C. hominis, C. meleagridis, C. andersoni, C. baileyi, C. bovis, C. canis, C. serpentis, and C. wrain*), 1 species of *Giardia* (*G. intestinalis*), and 2 species of microsporidia (*Encephalitozoon intestinalis* and *Enterocytozoon bieneusi*). Additionally, the above process was used to synthesize standards for the 18s rRNA genes of 5 species of *Cryptosporidium* (*C. hominis, C. parvum, C. muris, C. meleagridis*, and *C. felis*) and 1 species of *Giardia* (*G. intestinalis*). The PCR performance of these standards was then compared against that of genomic DNA from the target organisms using real-time PCR assays.

Prior to PCR amplification, synthetic standards were manufactured by a third-party. Native *C. parvum, C. hominis, C. meleagridis, C. muris* and *G. intestinalis* DNA was purchased from either ATCC or BEI Resources. Sample DNA concentrations (ng/μl) were converted to CN concentrations (CN/μl) based upon the CN densities calculated previously. Synthetic and native DNA samples were serially diluted in TE (10 mM Tris-HCl, 1 mM EDTA, pH 8.0) to obtain concentrations between 107 and 100 CN/μl.

PCR amplification was performed in triplicate using a real-time PCR assay optimized for the LightCycler 2.0. PCR amplification was confirmed by gel electrophoresis using the Invitrogen E-Gel® Ex (2% agarose) system.

Figure 2:
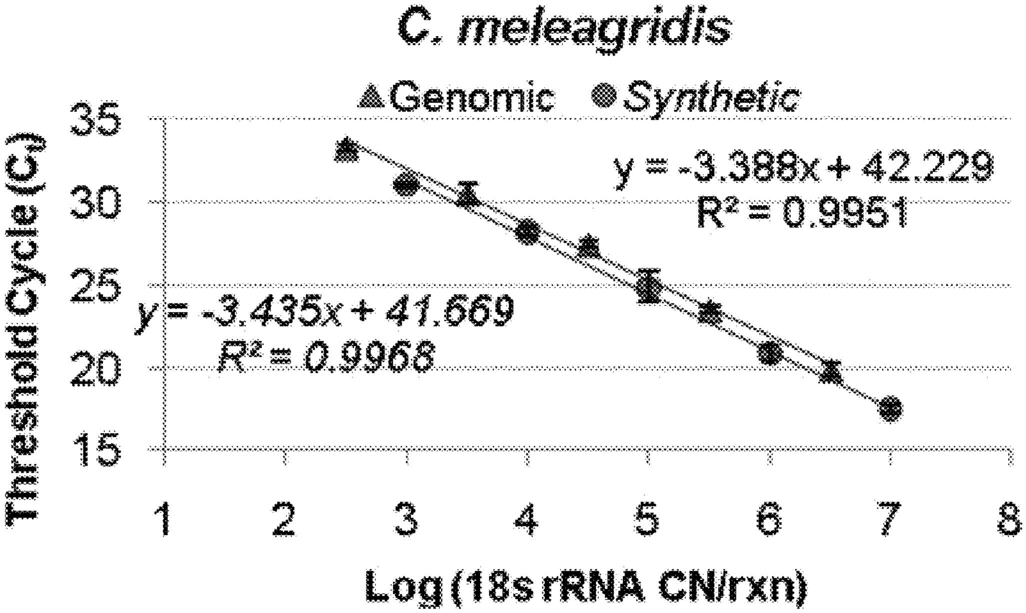
FIG. 2 shows standard curves of *C. meleagridis* genomic and synthetic target DNA in real-time PCR assays.
Figure 3:
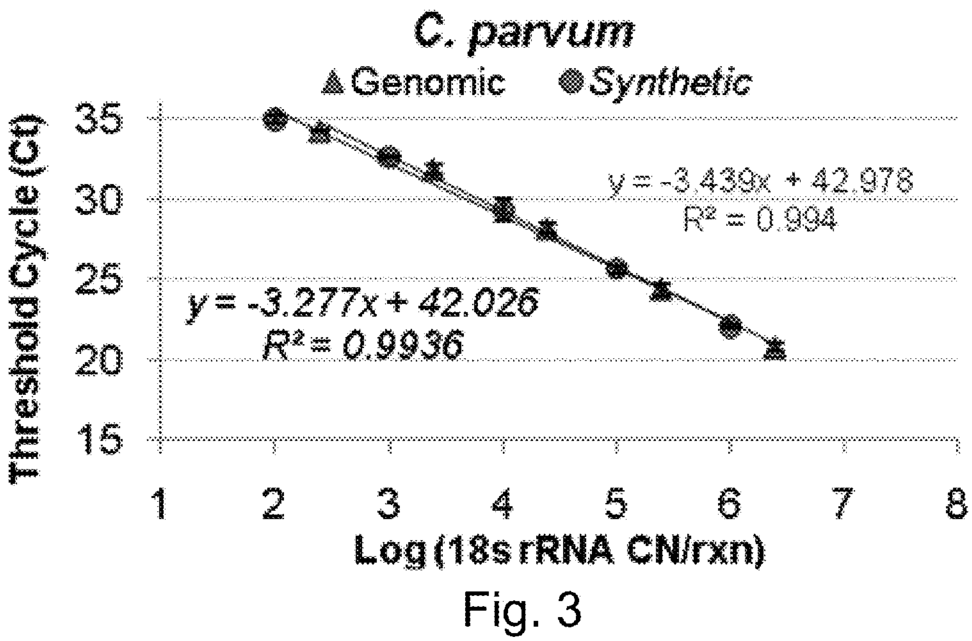
FIG. 3 shows standard curves of *C. parvum* genomic and synthetic target DNA in real-time PCR assays.
Figure 4:
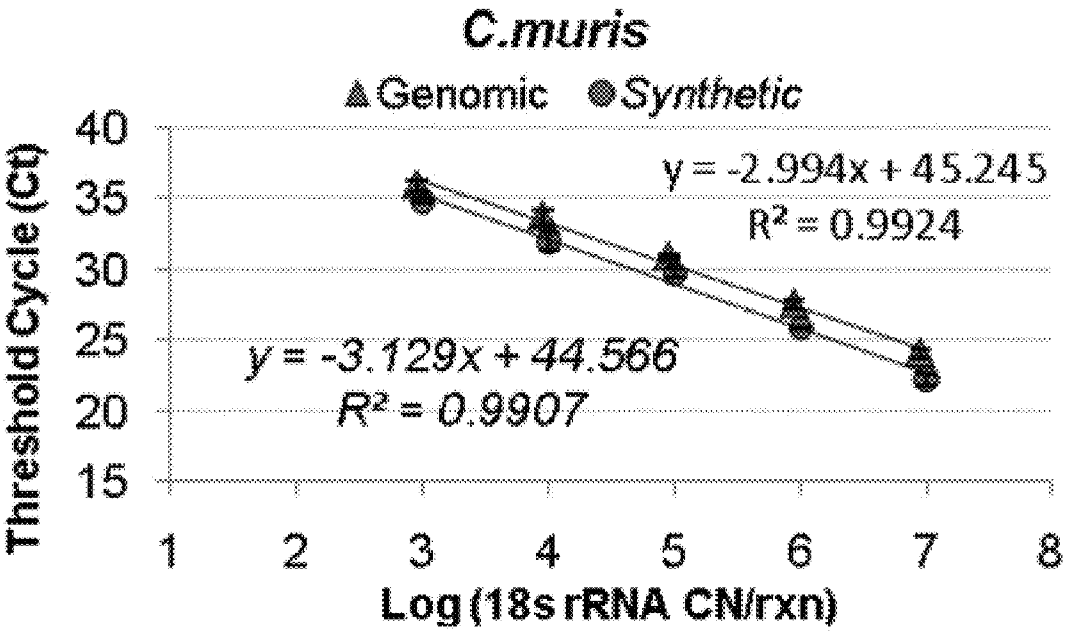
FIG. 4 shows standard curves of *C. muris* genomic and synthetic target DNA in real-time PCR assays.
Figure 5:
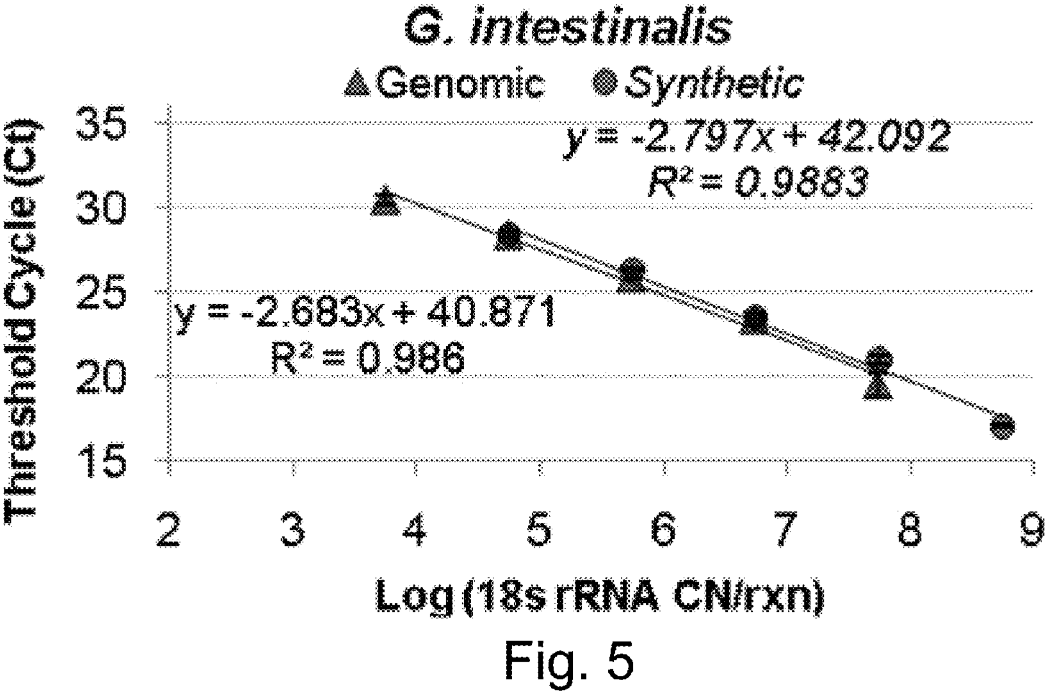
FIG. 5 shows standard curves of *G. intestinalis* genomic and synthetic target DNA in real-time PCR assays.
Figure 6:
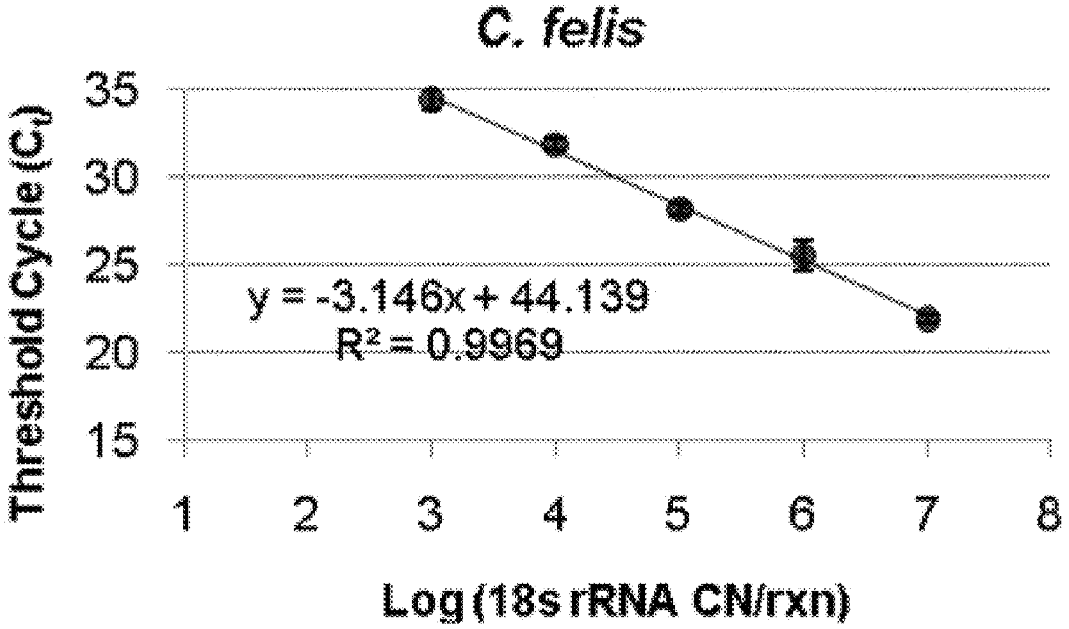
FIG. 6 shows standard curves of *C. felis* synthetic target DNA in real-time PCR assays.

FIGS. 1-6 show standard curves for each species. The standard curves were calculated by plotting PCR threshold cycle values ($C_t$) versus $\log_{10}$ (CN/rxn) for each DNA type. Linearity ($R^2$) and efficiency were calculated over at least 4 orders of magnitude using linear regression.

Standard curves generated using synthetic or native DNA demonstrated nearly identical $R^2$ values of approximately 0.99. For each species, the synthetic and native DNA demonstrated substantially equivalent PCR performance (Table 1), demonstrating that either could be used to construct an accurate standard curve for target quantification.

While the present disclosure has been described in terms of exemplary embodiments, those skilled in the art will recognize that the present disclosure can be practiced with (or without) modifications in the spirit and scope of the appended claims. The examples disclosed herein are merely illustrative and are not meant to be an exhaustive list of all possible designs, embodiments, applications or modifications of the present disclosure.

TABLE 1

Limit of Detection, Efficiency, and Linearity

| Organisms | Type | LOD (CN/rxn) | Efficiency (%) | $R^2$ | Δ Eff | Δ Tm |
|---|---|---|---|---|---|---|
| *C. hominis* | Genomic | 10 | 101.82% | 0.99229 | 2.07% | 0.09 |
| | Synthetic | 10 | 103.89% | 0.99466 | | |
| *C. parvum* | Genomic | 10 | 95.34% | 0.99397 | 6.57% | 0.31 |
| | Synthetic | 10 | 101.91% | 0.99355 | | |
| *C. meleagridis* | Genomic | 10 | 97.31% | 0.99513 | 1.83% | −0.15 |
| | Synthetic | 10 | 95.49% | 0.99677 | | |
| *C. muris* | Genomic | N/A | 115.78% | 0.99239 | 7.04% | N/A |
| | Synthetic | 10 | 108.73% | 0.99074 | | |
| *C. felis* | Synthetic | 10 | 107.90% | 0.99691 | N/A | N/A |
| *G. lamblia* | Genomic | 5500 | 135.89% | 0.98598 | 8.11% | |
| | Synthetic | 5500 | 127.79% | 0.98832 | | |

What is claimed is:

1. A method for constructing a consensus sequence from an alignment of a plurality of nucleic acid sequences, the method comprising:

generating a frequency matrix comprising the frequency of each base at each position in the alignment;

creating an information matrix comprising the amount of information provided by each base at each position in the alignment; and calculating an information score for each of the plurality of nucleic acid sequences;

iterating over each position in the alignment and for each position:

(a) calculating base frequencies and determining a highest frequency base;

(b) if the highest frequency base's frequency is higher than a frequency threshold, assigning the highest frequency base to the consensus sequence; and (c) if the highest frequency base's frequency is lower than the frequency threshold, removing a base corresponding to a nucleic acid sequence with a lowest information score and returning to (a); and performing a restriction fragment length polymorphism (RFLP) fingerprint of the constructed consensus sequence in silico.

2. The method of claim 1, further comprising removing insertions and deletions from the alignment of a plurality of nucleic acid sequences.

3. The method of claim 1, wherein creating an information matrix comprises calculating the decrease in Shannon uncertainty for each base at each position in the alignment; and calculating an information score comprises summing the decrease in Shannon uncertainty for each base in each of the plurality of nucleic acid sequences.

4. The method of claim 1, further comprising:

comparing a restriction fragment length polymorphism (RFLP) fingerprint of the constructed consensus sequence to a RFLP fingerprint of each of the plurality of nucleic acid sequences in the alignment;

determining an oligonucleotide to bind to the consensus sequence; and comparing the oligonucleotide binding to the constructed consensus sequence and to the plurality of nucleic acid sequences in the alignment based on at least one of a Gibb's free energy of hybridization, a melting temperature, and a binding position.

5. The method of claim 1, wherein the frequency threshold is 0.7.

6. A method for constructing a consensus sequence from an alignment of a plurality of nucleic acid sequences, the alignment comprising a plurality of alignment positions, the method comprising:

determining the plurality of nucleic acid sequences from a computer database;

generating a frequency matrix comprising the frequency of each base at each alignment position;

creating an information matrix comprising the amount of information provided by each base at each alignment position;

calculating an information score for each of the plurality of nucleic acid sequences; and iterating over the alignment and for each alignment position:

(a) determining a highest frequency base;

(b) if the highest frequency base's frequency is higher than a frequency threshold, assigning the highest frequency base to the consensus sequence;

(c) if the highest frequency base's frequency is lower than the frequency threshold, removing from the current alignment position a base corresponding to a nucleic acid sequence with a lowest information score, recalculating base frequencies for the current alignment position, and returning to (a); and performing a restriction fragment length polymorphism (RFLP) fingerprint of the constructed consensus sequence in silico.

7. The method of claim 6, further comprising removing insertions and deletions from the alignment of a plurality of nucleic acid sequences.

8. The method of claim 6, further comprising:

comparing a restriction fragment length polymorphism (RFLP) fingerprint of the constructed consensus sequence to a RFLP fingerprint of each of the plurality of nucleic acid sequences in the alignment; and comparing oligonucleotide binding to the constructed consensus sequence and to the plurality of nucleic acid sequences in the alignment based on at least one of a Gibb's free energy of hybridization, a melting temperature, and a binding position.

9. The method of claim 6, wherein creating an information matrix comprises calculating the decrease in Shannon uncertainty for each base at each position in the alignment; and calculating an information score comprises summing the decrease in Shannon uncertainty for each base in each of the plurality of nucleic acid sequences.

10. The method of claim 6, wherein the frequency threshold is 0.7.

* * * * *

SEQUENCE LISTING

<160> NUMBER OF SEQ ID NOS: 26

<210> SEQ ID NO 1
<211> LENGTH: 1745
<212> TYPE: DNA
<213> ORGANISM: Artificial Sequence
<220> FEATURE:
<223> OTHER INFORMATION: 18S rRNA Consensus Sequence for Cryptosporidium andersoni

<400> SEQUENCE: 1
aacctggttg atcctgcaag tagtcatatg cttgtctcaa agattaagcc atgcatgtct 60
aagtataagc ttttaaacgg cgaaactgcg aatggctcat taaaaaagtt attatttact 120
tgataatcca aaactacatg gataaccgtg gtaattctag agctaataca tgcgaaaaaa 180
cccaacttcg cggaagggtt gtatttatta gataaagaac caatgagctt ggtgattcat 240
aataacttta cggatcgcat ctctgatgcg acatatcatt caagtttctg acctatcagc 300
tttagacggt agggtattgg cctaccgtgg ctatgacggg taacggggaa ttagggttcg 360
attccggaga gggagcctga gaaacggcta ccacatctaa ggaaggcagc aggcgcgcaa 420
attacccaat cctgacacag ggaggtagtg acaagaaata acaatacagg gcctaacggt 480
cttgtaattg gaatgagtga agtataaacc cctttacgag tatcaattgg agggcaagtc 540
tggtgccagc agccgcggta attccagctc caatagcgta tattaaagtt gttgcagtta 600
aaaagctcgt agttggattt ctgttgtata attttataat attaccaagg taattattat 660
attatcaaca tccttcctat tatattctaa atatatagga aattttactt tgagaaaatt 720
agagtgctta aagcaggcaa ctgccttgaa tactccagca tggaataata agtaaggact 780
tttgtctttc ttattggttc taggacaaaa gtaatggtta atagggacag ttgggggcat 840
tcgtatttaa cagccagagg tgaaattctt agatttgtta aagacgaact actgcgaaag 900
catttgccaa ggatgttttc attaatcaag aacgaaagtt aggggatcga agacgatcag 960

-continued ataccgtcgt agtcttaacc ataaactatg ccgactagag attggaggtt gttccttact 1020
ccttcagcac cttatgagaa atcaaagttt ttgggttctg gggggagtat ggtcgcaagg 1080
ctgaaactta aaggaattga cggaagggca ccaccaggag tggagcctgc ggcttaattt 1140
gactcaacac gggaaaactc accaggtcca gacataggaa ggattgacag attgatagct 1200
ctttcttgat tctatgggtg gtggtgcatg gccgttctta gttggtggag tgatttgtct 1260
ggttaattcc gttaacgaac gagaccttaa cctgctaaat aggtaataga aattttattt 1320
ctatcttatc ttcttagagg gactttgcgt gcctaacgcg aggaagtttg aggcaataac 1380
aggtctgtga tgcccttaga tgtcctgggc cgcacgcgcg ctacactgat gcatccagcg 1440
agtatatatc ctgtttcgaa ggaaatgggt aatcttatga gtatgcatcg tgatggggat 1500
agatcattgc aattattgat ctttaacgag gaattcctag taagcgcaag tcatcagctt 1560
gcgctgatta cgtccctgcc ctttgtacac accgcccgtc gctcctaccg attgagtgat 1620
ccggtgaata attcggacca tgctacagta gcaaatacat agcaagggaa gtttcgtaaa 1680
ccttatcact tagaggaagg agaagtcgta acaaggtttc cgtaggtgaa cctgcagaag 1740
gatca 1745

<210> SEQ ID NO 2
<211> LENGTH: 1733
<212> TYPE: DNA
<213> ORGANISM: Artificial Sequence
<220> FEATURE:
<223> OTHER INFORMATION: 18S rRNA Consensus Sequence for Cryptosporidium baileyi

<400> SEQUENCE: 2
aacctggttg atcctgccag tagtcatatg cttgtctcaa agattaagcc atgcatgtct 60
aagtataagc ttctatacgg ctaaactgcg aatggctcat tataacagtt atagtttact 120
tgataatcct tactacatgg ataaccgtgg taattctaga gctaatacat gcgaaaagac 180
ccgacttctc ggaagggttg tatttattag ataaagaacc aatactcttg gtgactcata 240
ataactttac ggatcacatt tatgtgacat atcattcaag tttctgacct atcagcttta 300
gacggtaggg tattggccta ccgtggctat gacgggtaac ggggaattag ggttcgattc 360
cggagaggga gcctgagaaa cggctaccac atctaaggaa ggcagcaggc gcgcaaatta 420
cccaatcctg acacagggag gtagtgacaa gaaataacaa tacagggcct aacggtcttg 480
taattggaat gagttaagta taaacccctt tacaagtagc aattggaggg caagtctggt 540
gccagcagcc gcggtaattc cagctccaat agcgtatatt aaagttgttg cagttaaaaa 600
gctcgtagtt ggatttctgt taatacttat atacaatacc acggtattta tataacatta 660
acataattca cattacttat ttaaagtatg tgaaacttta ctttgagaaa attagagtgc 720
ttaaagcagg ctattgcctt gaatactcca gcatggaata atattaaaga tttttatctt 780
tcttattggt tctaggataa aaataatgat taatagggac agttgggggc atttgtattt 840
aacagtcaga ggtgaaattc ttagatttgt taaagacaaa ctactgcgaa agcatttgcc 900
aaggatgttt tcattaatca agaacgaaag ttaggggatc gaagacgatc agataccgtc 960
gtagtcttaa ccataaacta tgccgactag agattggagg ttgttcctta ctccttcagc 1020
accttatgag aaatcaaagt ctttgggttc tggggggagt atggtcgcaa ggctgaaact 1080
taaaggaatt gacggaaggg caccaccagg agtggagcct gcggcttaat ttgactcaac 1140
acgggaaaac tcaccaggtc cagacatagg aaggattgac agattgatag ctctttcttg 1200

-continued

```
attctatggg tggtggtgca tggccgttct tagttggtgg agtgatttgt ctggttaatt   1260

ccgttaacga acgagacctt aacctgctaa atagacataa gaaaattatt tcttatctgt   1320

cttcttagag ggactttgtg tgtttaacac gaggaagttt taggcaataa caggtctgtg   1380

atgcccttag atgtcctggg ccgcgcgcgc gctacactga tgtatccatc aagtattctc   1440

ctgtttcgaa ggaaatgggt aatcttatga atatacatcg tgatggggat agatcattgc   1500

aattattgat cttcaacgag gaattcctag taagcgcaag tcatcagctt gcgctgatta   1560

cgtccctgcc ctttgtacac accgcccgtc gctcctaccg attgagtgat ccggtgaatt   1620

attcggacca tacataagta gcaatacatg taaggaaagt tttgtaaacc ttatcactta   1680

gaggaaggag aagtcgtaac aaggtttccg taggtgaacc tgcagaagga tca          1733


<210> SEQ ID NO 3
<211> LENGTH: 1729
<212> TYPE: DNA
<213> ORGANISM: Artificial Sequence
<220> FEATURE:
<223> OTHER INFORMATION: 18S rRNA Consensus Sequence for Cryptosporidium
      bovis

<400> SEQUENCE: 3

aacctggttg atcctgccag tagtcatatg cttgtctcaa agattaagcc atgcatgtct     60

aagtataagc ttttatacag ctaaactgcg aatggctcat tataacagtt atagtttact    120

tgataatctt tactacatgg ataaccgtgg taattctaga gctaatacat gcgaaaaaac    180

ccgacttctt ggaagggttg tatttattag ataaagaacc aatatttttg gtgactcata    240

ataactttac ggatcacatt atgtgacata tcattcaagt ttctgaccta tcagctttag    300

acggtagggt attggcctac cgtggctatg acgggtaacg gggaattagg gttcgattcc    360

ggagagggag cctgagaaac ggctaccaca tctaaggaag gcagcaggcg cgcaaattac    420

ccaatcctaa tacagggagg tagtgacaag aaataacaat acagaacctt acggttttgt    480

aattggaatg agttaagtat aaacccctta acaagtatca attggagggc aagtctggtg    540

ccagcagccg cggtaattcc agctccaata gcgtatatta aagttgttgc agttaaaaag    600

ctcgtagtta atcttctgtt aatttttata tataatatca cgatatttat ataatattaa    660

cataattcat attacttttt agtatatgaa actttacttt gagaaaatta gagtgcttaa    720

agcaggctat tgccttgaat actccagcat ggaataatat taaggatttt tattcttctt    780

attggttcta gaataaaaat gatgattaat aggaacagtt gggggcattt gtatttaaca    840

gtcagaggtg aaattcttag atttgttaaa gacaaactac tgcgaaagca tttgccaagg    900

atgttttcat taatcaagaa cgaaagttag gggatcgaag acgatcagat accgtcgtag    960

tcttaaccat aaactatgcc aactagagat tggaggttgt tccttactcc ttcagcacct   1020

tatgagaaat caaagtcttt gggttctggg gggagtatgg tcgcaaggct gaaacttaaa   1080

ggaattgacg gaagggcacc accaggagtg gagcctgcgg cttaatttga ctcaacacgg   1140

gaaaactcac caggtccaga cataggaagg attgacagat tgatagctct ttcttgattc   1200

tatgggtggt ggtgcatggc cgttcttagt tggtggagtg atttgtctgg ttaattccgt   1260

taacgaacga gaccttaacc tgctaaatag acgtaaaaaa ttcgtttttt acctgtcttc   1320

ttagagggac tttgtgtgtt taacacgagg aagttttagg caataacagg tctgtgatgc   1380

ccttagatgt cctgggccgc gcgcgcgcta cactgatgca tccatcaagt tttctcctgc   1440

ttcgaaggaa gtgggtaatc ttttgaatat gcatcgtgat ggggatagaa cattgcaatt   1500

attgttcttc aacgaggaat tcctagtaag cgcaagtcat cagcttgcgc tgattacgtc   1560
```

-continued

```
cctgcccttt gtacacaccg cccgtcgctc ctaccgattg agtgatccgg tgaattattc   1620

ggaccatact ttgtagccaa tacatgtaag gaaagttttg taaaccttat cacttagagg   1680

aaggagaagt cgtaacaagg tttccgtagg tgaacctgca gaaggatca               1729
```

<210> SEQ ID NO 4
<211> LENGTH: 1742
<212> TYPE: DNA
<213> ORGANISM: Artificial Sequence
<220> FEATURE:
<223> OTHER INFORMATION: 18S rRNA Consensus Sequence for Cryptosporidium canis

<400> SEQUENCE: 4

```
aacctggttg atcctgccag tagtcatatg cttgtctcaa agattaagcc atgcatgtct     60

aagtataagc ttttatacgg ttaaactgcg aatggctcat tataacagtt atagtttact    120

tgataatctt tacttacatg gataaccgtg gtaattctag agctaataca tgcgaaaaaa    180

cctgactttt tggaaaggtt gtatttatta gataaagaac caatattttt ggtgattcat    240

aataacttta cggatcacat tttatgtgac atatcattca agtttctgac ctatcagctt    300

tagacggtag ggtattggcc taccgtggca atgacgggta acggggaatt agggttcgat    360

tccggagagg gagcctgaga aacggctacc acatctaagg aaggcagcag gcgcgcaaat    420

tacccaatcc taatacaggg aggtagtgac aagaaataac aatacaggac tttaacagtt    480

ttgtaattgg aatgagttga gtataaaccc ctttacaagt atcaattgga gggcaagtct    540

ggtgccagca gccgcggtaa ttccagctcc aatagcgtat attaaagttg ttgcagttaa    600

aaagctcgta gttggatttc tgttaataat ttatatataa tatttaacat atttatataa    660

tattaacata attcatatta ctatttatag tatatgaaac tttactttga gaaaattaga    720

gtgcttaaag caggcttttg ccttgaatac tagagcatgg aataatatta aagattttta    780

tctttcttat tggttctaag atagaaataa tgattaatag ggacagttgg gggcatttgt    840

atttaacagt tagaggtgaa attcttagat ttgttaaaga caaactaatg cgaaagcatt    900

tgccaaggat gttttcatta atcaagaacg aaagttaggg gatcgaagac gatcagatac    960

cgtcgtagtc ttaaccataa actatgccaa ctagagattg gaggttgttc ttttactcct   1020

tcagcacctt atgagaaatc aaagtctttg ggttctgggg ggagtatggt cgcaaggctg   1080

aaacttaaag gaattgacgg aagggcacca ccaggagtgg agcctgcggc ttaatttgac   1140

tcaacacggg aaaactcacc aggtccagac ataggaagga ttgacagatt gatagctctt   1200

tcttgattct atgggtggtg gtgcatggcc gttcttagtt ggtggagtga tttgtctggt   1260

taattccgtt aacgaacgag accttaacct gctaaataga catttgaaat atttttattt   1320

cttatttgtc ttcttagagg gactttgtat gtttaataca gggaagtttt aggcaataac   1380

aggtctgtga tgcccttaga tgtcctgggc cgcgcgcgcg ctacactgat gcatccatca   1440

agttttttc ctgtttcgaa ggaaatgggt aatcttttga atatgcatcg tgatggggat    1500

agatcattgc aattattgat cttgaacgag gaattcctag taagcgcaag tcatcagctt   1560

gcgctgatta cgtccctgcc ctttgtacac accgcccgtc gctcctaccg attgaatgat   1620

ccggtgaatt attcggacca tacgttgtag caatacatgt agggaaagtt tcgtaaacct   1680

tatcatttag aggaaggaga agtcgtaaca aggtttccgt aggtgaacct gcagaaggat   1740

ca                                                                  1742
```

<210> SEQ ID NO 5

-continued

<211> LENGTH: 1781
<212> TYPE: DNA
<213> ORGANISM: Artificial Sequence
<220> FEATURE:
<223> OTHER INFORMATION: 18S rRNA Consensus Sequence for Cryptosporidium felis

<400> SEQUENCE: 5

```
aacctggttg atcctgccag tagtcatatg cttgtctcaa agattaagcc atgcatgtct     60

aagtataaac ttttatacgg ttaaactgcg aatggctcat tataacagtt atagtttact    120

tgataatctt tttactacat ggataaccgt ggtaattcta gagctaatac atgcggaaag    180

accctacttt atggaaaggt cgtatttatt agataaagaa ccaatatttt tttttggtga    240

ctcataataa ctttacggat cacaataatt tattttgtga catatcattc aagtttctga    300

cctatcagct ttagacggta gggtattggc ctaccgtggc tatgacgggt aacggggaat    360

tagggttcga ttccggagag ggagcctgag aaacggctac cacatctaag gaaggcagca    420

ggcgcgcaaa ttacccaatc ctaatacagg gaggtagtga caagaaataa caatacagga    480

ctttacggtt ttgtaattgg aatgagttaa gtataaaccc ctttacaagt atcaattgga    540

gggcaagtct ggtgccagca gccgcggtaa ttccagctcc aatagcgtat attaaagttg    600

ttgcagttaa aaagctcgta gttggatttc tgttaatacc ttatatataa tatttttttt    660

taaatattat tatgtaagat taacataatt catatttttt aagactgaat tttagtttt    720

gataatatga aattttactt tgagaaaatt agagtgctta aagcaggctt ttgccttgaa    780

tactccagca tggaataata ataaaagatt tttatctttt ttttattggt tctaagataa    840

aaataatgat taatagggac agttgggggc atttgtattt aacagtcaga ggtgatattc    900

ttagatttgt taaagacaaa ctaatgcgaa agcatttgcc aaggatgttt tcattaatca    960

agaacgaaag ttaggggatc gaagacgatc agataccgtc gtagtcttaa ccataaacta   1020

tgccaactag agattggagg ttgttcctta ctccttcagc accttatgag aaatcaaagt   1080

ctttgggttc tgggggggagt atggtcgcaa ggctgaaact taaaggaatt gacggaaggg   1140

caccaccagg agtggagcct gcggcttaat ttgactcaac acgggaaaac tcaccaggtc   1200

cagacatagg aaggattgac agattgatag ctctttcttg attctatggg tggtggtgca   1260

tggccgttct tagttggtgg agtgatttgt ctggttaatt ccgttaacga acgagacctt   1320

aacctgctaa atagacataa gaaatatatt aatatttttt atttgtcttc ttagagggac   1380

tttgtatgtt taatacaggg aagttttagg caataacagg tctgtgatgc ccttagatgt   1440

cctgggccgc gcgcgcgcta cactgatgca tccgtcaagt atatttatcc tgtttcgaag   1500

gaaatgggta atcttttgaa tatgcatcgt gatggggata gatcattgca attattgatc   1560

tttaacgagg aattcctagt aagcgcaagt catcagcttg cgctgattac gtccctgccc   1620

tttgtacaca ccgcccgtcg ctcctaccga ttgaatgatc cggtgaatta ttcggaccat   1680

acaatgtagc aatacatgta aggaaagttt cgtaaacctt atcatttaga ggaaggagaa   1740

gtcgtaacaa ggtttccgta ggtgaacctg cggaaggatc a                       1781
```

<210> SEQ ID NO 6
<211> LENGTH: 1750
<212> TYPE: DNA
<213> ORGANISM: Artificial Sequence
<220> FEATURE:
<223> OTHER INFORMATION: 18S rRNA Consensus Sequence for Cryptosporidium hominis

<400> SEQUENCE: 6

-continued

```
aacctggttg atcctgccag tagtcatatg cttgtctcaa agattaagcc atgcatgtct     60

aagtataaac ttttatacgg ttaaactgcg aatggctcat tataacagtt atagtttact    120

tgataatctt ttacttacat ggataaccgt ggtaattcta gagctaatac atgcgaaaaa    180

actcgacttt atggaagggt tgtatttatt agataaagaa ccaatataat tggtgactca    240

taataacttt acggatcaca attaatgtga catatcattc aagtttctga cctatcagct    300

ttagacggta gggtattggc ctaccgtggc aatgacgggt aacggggaat tagggttcga    360

ttccggagag ggagcctgag aaacggctac cacatctaag gaaggcagca ggcgcgcaaa    420

ttacccaatc ctaatacagg gaggtagtga caagaaataa caatacagga ctttttggtt    480

ttgtaattgg aatgagttaa gtataaaccc ctttacaagt atcaattgga gggcaagtct    540

ggtgccagca gccgcggtaa ttccagctcc aatagcgtat attaaagttg ttgcagttaa    600

aaagctcgta gttggatttc tgttaataat ttatataaaa tattttgatg aatatttata    660

taatattaac ataattcata ttactatttt ttttttagt atatgaaatt ttactttgag     720

aaaattagag tgcttaaagc aggcatatgc cttgaatact ccagcatgga ataatattaa    780

agatttttat ctttttattt ggttctaaga taagaataat gattaatagg gacagttggg    840

ggcatttgta tttaacagtc agaggtgaaa ttcttagatt tgttaaagac aaactaatgc    900

gaaagcattt gccaaggatg ttttcattaa tcaagaacga aagttagggg atcgaagacg    960

atcagatacc gtcgtagtct taaccataaa ctatgccaac tagagattgg aggttgttcc   1020

ttactccttc agcaccttat gagaaatcaa agtctttggg ttctgggggg agtatggtcg   1080

caaggctgaa acttaaagga attgacggaa gggcaccacc aggagtggag cctgcggctt   1140

aatttgactc aacacgggaa aactcaccag gtccagacat aggaaggatt gacagattga   1200

tagctctttc ttgattctat gggtggtggt gcatggccgt tcttagttgg tggagtgatt   1260

tgtctggtta attccgttaa cgaacgagac cttaacctgc taaatagaca taagaaatat   1320

tatatttttt atctgtcttc ttagagggac tttgtatgtt taatacaggg aagttttagg   1380

caataacagg tctgtgatgc ccttagatgt cctgggccgc gcgcgcgcta cactgatgca   1440

tccatcaagt atatattcct gtttcgaagg aaatgggtaa tcttttgaat atgcatcgtg   1500

atggggatag atcattgcaa ttattgatct tgaacgagga attcctagta agcgcaagtc   1560

atcagcttgc gctgattacg tccctgccct ttgtacacac cgcccgtcgc tcctaccgat   1620

tgaatgatcc ggtgaattat tcggaccata ctttgtagca atacatgtaa ggaaagtttc   1680

gtaaacctta tcatttagag gaaggagaag tcgtaacaag gtttccgtag gtgaacctgc   1740

agaaggatca                                                          1750
```

```
<210> SEQ ID NO 7
<211> LENGTH: 1744
<212> TYPE: DNA
<213> ORGANISM: Artificial Sequence
<220> FEATURE:
<223> OTHER INFORMATION: 18S rRNA Consensus Sequence for Cryptosporidium
      meleagridis

<400> SEQUENCE: 7

aacctggttg atcctgccag tagtcatatg cttgtctcaa agattaagcc atgcatgtct     60

aagtataaac ttttatacgg ttaaactgcg aatggctcat tataacagtt atagtttact    120

tgataatctt tacttacatg gataaccgtg gtaattctag agctaataca tgcgaaaaaa    180

cctgacttaa tggaagggtt gtatttatta gataaagaac caatataatt ggtgactcat    240

aataacttta cggatcacaa tttatgtgac atatcattca agtttctgac ctatcagctt    300
```

```
tagacggtag ggtattggcc taccgtggca atgacgggta acggggaatt agggttcgat    360
tccggagagg gagcctgaga aacggctacc acatctaagg aaggcagcag gcgcgcaaat    420
tacccaatcc taatacaggg aggtagtgac aagaaataac aatacaggac tttttggttt    480
tgtaattgga atgagttaag tataaacccc tttacaagta tcaattggag ggcaagtctg    540
gtgccagcag ccgcggtaat tccagctcca atagcgtata ttaaagttgt tgcagttaaa    600
aagctcgtag ttggatttct gttaataatt tatatataat atttgattaa tatttatata    660
atattaacat aattcatatt actaaattta ttagtatatg aaattttact ttgagaaaat    720
tagagtgctt aaagcaggca tatgccttga atactccagc atggaataat attaaagatt    780
tttatctttc ttattggttc taagataaaa ataatgatta atagggacag ttgggggcat    840
ttgtatttaa cagtcagagg tgaaattctt agatttgtta aagacaaact aatgcgaaag    900
catttgccaa ggatgttttc attaatcaag aacgaaagtt aggggatcga agacgatcag    960
ataccgtcgt agtcttaacc ataaactatg ccaactagag attggaggtt gttccttact   1020
ccttcagcac cttatgagaa atcaaagtct ttgggttctg gggggagtat ggtcgcaagg   1080
ctgaaactta aaggaattga cggaagggca ccaccaggag tggagcctgc ggcttaattt   1140
gactcaacac gggaaaactc accaggtcca gacataggaa ggattgacag attgatagct   1200
ctttcttgat tctatgggtg gtggtgcatg gccgttctta gttggtggag tgatttgtct   1260
ggttaattcc gttaacgaac gagaccttaa cctgctaaat agacataaga aatattatat   1320
tttttatttg tcttcttaga gggactttgt atgtttaata cagggaagtt ttaggcaata   1380
acaggtctgt gatgccctta gatgtcctgg gccgcgcgcg cgctacactg atgcatccat   1440
caagtaataa tcctgtttcg aaggaaatgg gtaatctttt gaatatgcat cgtgatgggg   1500
atagatcatt gcaattattg atcttgaacg aggaattcct agtaagcgca agtcatcagc   1560
ttgcgctgat tacgtccctg ccctttgtac acaccgcccg tcgctcctac cgattgaatg   1620
atccggtgaa ttattcggac catactttgt agcaatacat gtaaggaaag tttcgtaaac   1680
cttatcattt agaggaagga gaagtcgtaa caaggtttcc gtaggtgaac ctgcagaagg   1740
atca                                                                1744
```

<210> SEQ ID NO 8
<211> LENGTH: 1746
<212> TYPE: DNA
<213> ORGANISM: Artificial Sequence
<220> FEATURE:
<223> OTHER INFORMATION: 18S rRNA Consensus Sequence for Cryptosporidium muris

<400> SEQUENCE: 8

```
aacctggttg atcctgccag tagtcatatg cttgtctcaa agattaagcc atgcatgtct     60
aagtataagc ttttatacgg cgaaactgcg aatggctcat taaaacagtt atagtttact    120
tgataatcaa aactacatgg ataaccgtgg taattctaga gctaatacat gcgaaaaaac    180
ccaactttgc ggaagggttg tatttattag ataaagaacc aatgagcttg gtgattcata    240
ataactttac ggatcgcatc tctgatgcga catatcattc aagtttctga cctatcagct    300
ttagacggta gggtattggc ctaccgtggc tatgacgggt aacggggaat tagggttcga    360
ttccggagag ggagcctgag aaacggctac cacatctaag gaaggcagca ggcgcgcaaa    420
ttacccaatc ctgacacagg gaggtagtga caagaaataa caatacaggg cctaacggtc    480
ttgtaattgg aatgagtgaa gtataaaccc ctttacgagt atcaattgga gggcaagtct    540
```

-continued

```
ggtgccagca gccgcggtaa ttccagctcc aatagcgtat attaaagttg ttgcagttaa    600

aaagctcgta gttggatttc tgttgtataa tctataatat tactaaggta tatattatat    660

tatcaacatc cttcctatta tatttctaaa tatataggaa actttacttt gagaaaatta    720

gagtgcttaa agcaggcaac tgccttgaat actccagcat ggaataataa gtaaggactt    780

ttgtctttct tattggttct aggacaaaag taatggttaa tagggacagt tgggggcatt    840

cgtatttaac agccagaggt gaaattctta gatttgttaa agacgaacta ctgcgaaagc    900

atttgccaag gatgttttca ttaatcaaga acgaaagtta ggggatcgaa gacgatcaga    960

taccgtcgta gtcttaacca taaactatgc cgactagaga ttggaggttg ttccttactc   1020

cttcagcacc ttatgagaaa tcaaagtctt tgggttctgg ggggagtatg gtcgcaaggc   1080

tgaaacttaa aggaattgac ggaagggcac caccaggagt ggagcctgcg gcttaatttg   1140

actcaacacg ggaaaactca ccaggtccag acataggaag gattgacaga ttgatagctc   1200

tttcttgatt ctatgggtgg tggtgcatgg ccgttcttag ttggtggagt gatttgtctg   1260

gttaattccg ttaacgaacg agaccttaac ctgctaaata ggtaatagaa atttattttt   1320

ctatattatc ttcttagagg gactttgcgt gtctaacgcg aggaagtttg aggcaataac   1380

aggtctgtga tgcccttaga tgtcctgggc cgcacgcgcg ctacactgat gcatccaacg   1440

agtatatatc ctgcttcgaa ggaagtgggt aatcttatga gtatgcatcg tgatggggat   1500

agatcattgt aattattgat ctttaacgag gaattcctag taagcgcaag tcatcagctt   1560

gcgctgatta cgtccctgcc ctttgtacac accgcccgtc gctcctaccg attgagtgat   1620

ccggtgaata attcggacca tgctacgagt agcaaataca tagcaaggaa agtttcgtaa   1680

accttatcac ttagaggaag gagaagtcgt aacaaggttt ccgtaggtga acctgcggaa   1740

ggatca                                                              1746


<210> SEQ ID NO 9
<211> LENGTH: 1748
<212> TYPE: DNA
<213> ORGANISM: Artificial Sequence
<220> FEATURE:
<223> OTHER INFORMATION: 18S rRNA Consensus Sequence for Cryptosporidium
      parvum

<400> SEQUENCE: 9

aacctggttg atcctgccag tagtcatatg cttgtctcaa agattaagcc atgcatgtct     60

aagtataaac ttttatacgg ttaaactgcg aatggctcat tataacagtt atagtttact    120

tgataatctt ttacttacat ggataaccgt ggtaattcta gagctaatac atgcgaaaaa    180

actcgacttt atggaagggt tgtatttatt agataaagaa ccaatataat tggtgactca    240

taataacttt acggatcaca ttaaatgtga catatcattc aagtttctga cctatcagct    300

ttagacggta gggtattggc ctaccgtggc aatgacgggt aacggggaat tagggttcga    360

ttccggagag ggagcctgag aaacggctac cacatctaag gaaggcagca ggcgcgcaaa    420

ttacccaatc ctaatacagg gaggtagtga caagaaataa caatacagga ctttttggtt    480

ttgtaattgg aatgagttaa gtataaaccc ctttacaagt atcaattgga gggcaagtct    540

ggtgccagca gccgcggtaa ttccagctcc aatagcgtat attaaagttg ttgcagttaa    600

aaagctcgta gttggatttc tgttaataat ttatataaaa tattttgatg aatatttata    660

taatattaac ataattcata ttactatata tttttagtat atgaaatttt actttgagaa    720

aattagagtg cttaaagcag gcatatgcct tgaatactcc agcatggaat aatattaaag    780

atttttatct ttcttattgg ttctaagata agaataatga ttaataggga cagttggggg    840
```

```
catttgtatt taacagtcag aggtgaaatt cttagatttg ttaaagacaa actaatgcga    900

aagcatttgc caaggatgtt ttcattaatc aagaacgaaa gttaggggat cgaagacgat    960

cagataccgt cgtagtctta accataaact atgccaacta gagattggag gttgttcctt   1020

actccttcag caccttatga gaaatcaaag tctttgggtt ctgggggag tatggtcgca   1080

aggctgaaac ttaaaggaat tgacggaagg gcaccaccag gagtggagcc tgcggcttaa   1140

tttgactcaa cacgggaaaa ctcaccaggt ccagacatag gaaggattga cagattgata   1200

gctctttctt gattctatgg gtggtggtgc atggccgttc ttagttggtg gagtgatttg   1260

tctggttaat tccgttaacg aacgagacct taacctgcta aatagacata agaaatatta   1320

tatttttat ctgtcttctt agagggactt tgtatgttta atacagggaa gttttaggca   1380

ataacaggtc tgtgatgccc ttagatgtcc tgggccgcgc gcgcgctaca ctgatgcatc   1440

catcaagtat atattcctgt ttcgaaggaa atgggtaatc ttttgaatat gcatcgtgat   1500

ggggatagat cattgcaatt attgatcttg aacgaggaat tcctagtaag cgcaagtcat   1560

cagcttgcgc tgattacgtc cctgcccttt gtacacaccg cccgtcgctc ctaccgattg   1620

aatgatccgg tgaattattc ggaccatact ttgtagcaat acatgtaagg aaagtttcgt   1680

aaaccttatc atttagagga aggagaagtc gtaacaaggt ctccgtaggt gaacctgcag   1740

aaggatca                                                            1748
```

```
<210> SEQ ID NO 10
<211> LENGTH: 1745
<212> TYPE: DNA
<213> ORGANISM: Artificial Sequence
<220> FEATURE:
<223> OTHER INFORMATION: 18S rRNA Consensus Sequence for Cryptosporidium
      serpentis

<400> SEQUENCE: 10

aacctggttg atcctgccag tagtcatatg cttgtctcaa agattaagcc atgcatgtct     60

aagtataagc ttttatacgg cgaaactgcg aatggctcat taaaacagtt atagtttact    120

tgataatcaa aactacatgg ataaccgtgg taattctaga gctaatacat gcgaaaaggc    180

ccgacttttt ggaagggttg tatttattag ataaagaacc aatattttttg gtgattcata    240

ataactttac ggatcgcatc tctgatgcga catatcattc aagtttctga cctatcagct    300

ttagacggta gggtattggc ctaccgtggc tatgacgggt aacggggaat tagggttcga    360

ttccggagag ggagcctgag aaacggctac cacatctaag gaaggcagca ggcgcgcaaa    420

ttacccaatc ctgacacagg gaggtagtga caagaaataa caatacaggg cctaacggtc    480

ttgtaattgg aatgagtgaa gtataaaccc ctttacaagt atcaattgga gggcaagtct    540

ggtgccagca gccgcggtaa ttccagctcc aatagcgtat attaaagttg ttgcagttaa    600

aaagctcgta gttggatttc tgttgtattt ttataatatt attaaggtaa tatttataat    660

atcaacatcc ttcctattat atttttaata tataggaaat tttactttga gaaaattaga    720

gtgcttaaag caggcaactg ccttgaatac tccagcatgg aataataagt aaggactttt    780

gtctttcttg ttggttctag gataaaagta atggttaata gggacagttg gggcattcg    840

tatttaacag tcagaggtga aattcttaga tttgttaaag acgaactact gcgaaagcat    900

ttgccaagga tgttttcatt aatcaagaac gaaagttagg ggatcgaaga cgatcagata    960

ccgtcgtagt cttaaccata aactatgccg actagagatt ggaggtgttg ttccttactc   1020

cttcagcacc ttatgagaaa tcaaagtctt tgggttctgg ggggagtatg gtcgcaaggc   1080
```

-continued

```
tgaaacttaa aggaattgac ggaagggcac caccaggagt ggagcctgcg gcttaatttg   1140

actcaacacg ggaaaactca ccaggtccag acataggaag gattgacaga ttgatagctc   1200

tttcttgatt ctatgggtgg tggtgcatgg ccgttcttag ttggtggagt gatttgtctg   1260

gttaattccg ttaacgaacg agaccttaac ctgctaaata gataataaaa atttattttt   1320

ttattttatc ttcttagagg gactttgcgt gtctaacgcg aggaagtttg aggcaataac   1380

aggtctgtga tgcccttaga tgtcctgggc cgcacgcgcg ctacactgat gcatccagcg   1440

agtatatatc ctgtttcgaa ggaaatgggt aatcttgtga gtatgcatcg tgatggggat   1500

agatcattgc aattattgat ctttaacgag gaattcctag taagcgcaag tcatcagctt   1560

gcgctgatta cgtccctgcc ctttgtacac accgcccgtc gctcctaccg attgagtgat   1620

ccggtgaata attcggacca tgctatagta gcaaatacat agtaaggaaa gtttcgtaaa   1680

ccttatcact tagaggaagg agaagtcgta acaaggtttc cgtaggtgaa cctgcagaag   1740

gatca                                                               1745
```

<210> SEQ ID NO 11
<211> LENGTH: 1746
<212> TYPE: DNA
<213> ORGANISM: Artificial Sequence
<220> FEATURE:
<223> OTHER INFORMATION: 18S rRNA Consensus Sequence for Cryptosporidium wrairi

<400> SEQUENCE: 11

```
aacctggttg atcctgccag tagtcatatg cttgtctcaa agattaagcc atgcatgtct     60

aagtataaac ttttatacgg ttaaactgcg aatggctcat tataacagtt atagtttact    120

tgataatctt tacttacatg gataaccgtg gtaattctag agctaataca tgcgaaaagg    180

cccgacttta tggaagggtt gtatttatta gataaagaac caatataatt ggtgactcat    240

aataacttta cggatcacat aaattgtgac atatcattca agtttctgac ctatcagctt    300

tagacggtag ggtattggcc taccgtggca atgacgggta acggggaatt agggttcgat    360

tccggagagg gagcctgaga aacggctacc acatctaagg aaggcagcag gcgcgcaaat    420

tacccaatcc taatacaggg aggtagtgac aagaaataac aatacaggac tttttggttt    480

tgtaattgga atgagttaag tataaacccc tttacaagta tcaattggag ggcaagtctg    540

gtgccagcag ccgcggtaat tccagctcca atagcgtata ttaaagttgt tgcagttaaa    600

aagctcgtag ttggatttct gttaataatt tatatataat attttgaaaa tatttatata    660

atattaacat aattcatatt actatatatt tttagtatat gaaattttac tttgagaaaa    720

ttagagtgct taaagcaggc atatgccttg aatactccag catggaataa tattaaagat    780

ttttatcttt cttattggtt ctaagataag aataatgatt aatagggaca gttgggggca    840

tttgtattta acagtcagag gtgaaattct tagatttgtt aaagacaaac tagtgcgaaa    900

gcatttgcca aggatgtttt cattaatcaa gaacgaaagt taggggatcg aagacgatca    960

gataccgtcg tagtcttaac cataaactat gccaactaga gattggaggt tgttccttac   1020

tccttcagca ccttatgaga aatcaaagtc tttgggttct ggggggagta tggtcgcaag   1080

gctgaaactt aaaggaattg acggaagggc accaccagga gtggagcctg cggcttaatt   1140

tgactcaaca cgggaaaact caccaggtcc agacatagga aggattgaca gattgatagc   1200

tctttcttga ttctatgggt ggtggtgcat ggccgttctt agttggtgga gtgatttgtc   1260

tggttaattc cgttaacgaa cgagacctta acctgctaaa tagacataag aaatattata   1320

ttttttatct gtcttcttag agggactttg tatgtttaat acagggaagt tttaggcaat   1380
```

-continued aacaggtctg tgatgccctt agatgtcctg ggccgcgcgc gcgctacact gatgcatcca 1440
tcaagtatat attcctgttt cgaaggaaat gggtaatctt ttgaatatgc atcgtgatgg 1500
ggatagatca ttgcaattat tgatcttgaa cgaggaattc ctagtaagcg caagtcatca 1560
gcttgcgctg attacgtccc tgccctttgt acacaccgcc cgtcgctcct accgattgaa 1620
tgatccggtg aattattcgg accatacttt gtagcaatac atgtaaggaa agtttcgtaa 1680
accttatcat ttagaggaag gagaagtcgt aacaaggttt ccgtaggtga acctgcagaa 1740
ggatca 1746

<210> SEQ ID NO 12
<211> LENGTH: 1783
<212> TYPE: DNA
<213> ORGANISM: Artificial Sequence
<220> FEATURE:
<223> OTHER INFORMATION: 18S rRNA Consensus Sequence for Giardia intestinalis

<400> SEQUENCE: 12
ataaatggac tcccgccgcc gtacgggctc gggcctccgt cacgcactat ataggacaag 60
gtgctttatc tcgccgaggc cggtttttttg gactggccca agagtcccca agggaatcca 120
aaaaaatgtg gtgcagacgg actcccgccg ccgtgcgggc gccgccctgc gtcccgcact 180 atagggggacc ccccgacccg gaccgcgccg cgagggggcg gccccccgtgc cccgcggcgg 240 cgcccgcgca gggcggcccg caggccccgg cgcccgcgcc cggccatccg gtcgatcctg 300
ccggaatccg acgctctccc caaggacaaa gccatgcatg cccgcgcacc cgggaggcgg 360
cggacggctc aggacaacgg ttgcaccccc cgcggcggtc cctgctagcc ggacaccgct 420
ggcaacccgg cgccaagacg tgcgcgcaag ggcgggcgcc cgcgggcgag cagcgtgacg 480
cagcgacggc ccgcccgggc ttccggggca tcacccggtc ggcgcggtcg cggcgcgccg 540
agggcccgac gcctggcgga gaatcagggt tcgactccgg agagcgggcc tgagagacgg 600
cccgcacatc caaggacggc agcaggcgcg gaacttgccc aatgcgcggc gcgcgaggca 660
gcgacgggga gtgcgcgagc gaggcgggcc cacagccccc gccgcggagc cgagggcaag 720
gtctggtgcc agcagccgcg gtaattccag ctcggcgggc gtcgcgtggc gctgctgcag 780
ttaaaacgcc cgtagttggc cccccgccgc cacgaggaaa cgggagcgct ccaggcaggc 840
ccgttggacc cgccgcgtgg gaccgcgcag cgggcgcggc gcgccgcggc agccccgagg 900
agagcgggcg ggggcaccgg taccggccgg ggacgggtga aacaggatga tcccgccgag 960
accgccggcc gcgcaggcgc ctgccaagac cgcctctgtc aatcaagggc gaaggccggg 1020
ggctagaagg cgatcagaca ccaccgtatt cccggccgta aacggtgccg ccccgcggcc 1080
ggcgcgcgcg tcccgccggc cgcccaggga aaccgggagg ctccgggctc tggggggagt 1140
atggccgcaa ggctgaaact tgaaggcatt gacggagggg taccaccaga cgtggagtct 1200
gcggctcaat ctgactcaac gcgcgcacct caccaggccc ggacgcgcgg aggaccgaca 1260
gccgggcgcg ctttcgcgat cgcgcgggcg gtggtgcatg gccgctccca gcccgtggcg 1320
cgagccgtct gctccattgc gacaacgagc gagaccccgg ccgcgggcgc cgcgggacgg 1380
cccgcgcgag cgggaggacg gcggggcgat agcaggtctg tgatgccctc agacgccctg 1440
ggccgcacgc gcgctacact ggcggggcca gccggcgccc gcgaggacgc gcggagcccc 1500
cgccgtggcc gggaccgcgg gctggaacgc ccccgcgcac caggaatgtc ttgtaggcgc 1560
gcgcccccac cgcgcgccgg acgcgtccct gccccttgta cacaccgccc gtcgctccta 1620

-continued

```
ccgactgggc gcggcggcga gcgccccgga cgcgcgaagg gccgcgagcc cccgcgcctg   1680

gaggaaggag aagtcgtaac aaggtatccg taggtgaacc tgcggatgga tccctcgcgc   1740

gcgcggcgtg cgtccccgcg gcccggtcgg cacgcgagcc ccg                     1783


<210> SEQ ID NO 13
<211> LENGTH: 1300
<212> TYPE: DNA
<213> ORGANISM: Artificial Sequence
<220> FEATURE:
<223> OTHER INFORMATION: 18S rRNA Consensus Sequence for Encephalitozoon
      intestinalis

<400> SEQUENCE: 13

tcaccaggtt gattctgcct gacgtggatg ctattctctg ggactaagcc atgcatgttg     60

atgaaccttg tgggggattg acggacggct cagtgatagt acgatgattt ggttggcggg    120

agagctgtaa ctgcgggaaa ctgcaggtag ggggctagga gtgtttttga cacgagccaa    180

gtaagttgta ggcctatcag ctggtagtta gggtaatggc ctaactaggc ggagacggga    240

gacgggggat cggggtttga ttccggagag ggagcctgag agatggctac tacgtccaag    300

gatggcagca ggcgcgaaac ttgcctaatc ctttggggag gcggttatga gaagtgagtt    360

tttttcgagt gtaaaggagt cgagattgat tggagggcaa gtcgggtgcc agcagccgcg    420

gtaatacctg ctccaatagt gtctatggtg aatgctgcag ttaaaaagtc cgtagtcttt    480

tgtatgtctt tgtttggggg attatgtcct gatgtggatg taagaggttt ggcagaggac    540

gaggggcacc ggatagttgg gcgaggggtg aaatacgaag accctgactg gacggacaga    600

agcgaaggct gtgctcttgg acttatgtga cgatgaagga cgaaggctag aggatcgaaa    660

tcgattagat accgttttag ttctagcagt aaacgatgcc gactggacgg gactatatag    720

tgttgtgcat gagaaatctt gagtatgtgg gttctgggga tagtatgctc gcaagagtga    780

aacttgaaga gattgacgga aggacaccac aaggagtgga gtgtgcggct taatttgact    840

caacgcgggg caacttaccg gttctgaagc gggcaggaga acgaggacgg gatgcgcgcg    900

gcggtggtgc atggccgttt gaaatggatg gcgtgagctt tggattaagt tgcgtaagat    960

gtgagaccct ttgacagtgc tctttggggc aagggaggaa tggaacagaa caggtccgtt   1020

atgccctgag atgaagcggg cggcacgcgc actacgatag atggcgaggg agcctgctgt   1080

gagggatgaa gctgtgtaat gggcttctga acgtggaatt cctagtaata acgattgaac   1140

aagttgtttt gaatgggtcc ctgtcctttg tacacaccgc ccgtcgctat ctaagatgac   1200

gcagtggacg aagattggaa ggtctgagtc cttcgtgtta gataagatat aagtcgtaac   1260

atggctgctg ttggagaacc agcagcagga tcagtatttg                         1300


<210> SEQ ID NO 14
<211> LENGTH: 1298
<212> TYPE: DNA
<213> ORGANISM: Artificial Sequence
<220> FEATURE:
<223> OTHER INFORMATION: 18S rRNA Consensus Sequence for Enterocytozoon
      bieneusi

<400> SEQUENCE: 14

gcattaggtt gattctgcct aacgtagatg ctagtctctg agattaagcc atgcatgtca     60

gtgaagcctt acggtggaac ggcgaacggc tcagtaatgt tgcggtaatt tggtctctgt    120

gtgtaaacta accacggtaa cctgtggcta aaagcgagaa taaggcgcaa ccctatcagc    180

ttgttggtag tgtaaaggac taccaaggcc atgacgggta acgggaaatc agggtttgat    240
```

-continued

```
tccggagagg gagcctgaga gatggctccc acgtccaagg acggcagcag gcgcgaaact    300

tgtccactcc ttacgggga gacagtcatg agacgtgagt ataagacctg agtgtaaaga    360

ccttagggtg aagcaattgg agggcaagct ttggtgccag cagccgcggt aactccaact    420

ccaagagtgt ctatggtgga tgctgcagtt aaagggtccg tagtcgtgaa tgcaattaaa    480

tgtcgttgtt caatagcgat gagtttgcta atgtttgcgg aacggatagg gagtgtagta    540

tagactggcg aagaatgaaa tctcaagacc cagtttggac taacggaggc gaaggcgaca    600

ctcttagacg tatcttagga tcaaggacga aggcaggagt atcgaaagtg attagacacc    660

gctgtagttc ctgcagtaaa ctatgccgac agcctgtgtg tgagaatacg tgggcgggag    720

aaatcttagt gttcgggctc tggggatagt acgctcgcaa gggtgaaact taaagcgaaa    780

ttgacggaag gacactacca ggagtggatt gtgctgctta atttaactca acgcgggaaa    840

acttaccagg gtcaagtcat tcgttgatcg aatacgtgag aatggcagga gtggtgcatg    900

gccgttggaa attgatgggg cgacctttag cttaaatgct taaaccagtg agacctcctt    960

gacaggtgtt ctgtaacaca ggagggtgga ggctataaca ggtccgtgat gcccttagat   1020

atcctgggca gcaagcgcaa tacaatatct cttcagtaga caaagtgatt tgagatgagt   1080

aggatctacg tttgtaaata cgtagtgaat aaggaattcc tagtaacggt gcctcatcaa   1140

ggcatggtga atgtgtccct gttctttgta cacaccgccc gtcactattt cagatggtca   1200

tagggatgaa gagcttcggc tctgaatatc tatggctaga taaagtacaa gtcgtaacaa   1260

ggtttcagtt ggagaaccag ctgaaggatc attttcag                            1298
```

<210> SEQ ID NO 15
<211> LENGTH: 38
<212> TYPE: DNA
<213> ORGANISM: Artificial Sequence
<220> FEATURE:
<223> OTHER INFORMATION: 18s rRNA gene

<400> SEQUENCE: 15
actggtagct agcctggatc gatcgggtgt agtactga 38

<210> SEQ ID NO 16
<211> LENGTH: 16
<212> TYPE: DNA
<213> ORGANISM: Artificial Sequence
<220> FEATURE:
<223> OTHER INFORMATION: 18s rRNA gene

<400> SEQUENCE: 16
tagcctggat ccatcg 16

<210> SEQ ID NO 17
<211> LENGTH: 9
<212> TYPE: DNA
<213> ORGANISM: Artificial Sequence
<220> FEATURE:
<223> OTHER INFORMATION: 18s rRNA gene

<400> SEQUENCE: 17 tattactga 9

<210> SEQ ID NO 18
<211> LENGTH: 15
<212> TYPE: DNA
<213> ORGANISM: Artificial Sequence
<220> FEATURE:
<223> OTHER INFORMATION: 18s rRNA gene -continued

<400> SEQUENCE: 18
taggtagcct ggatc 15

<210> SEQ ID NO 19
<211> LENGTH: 38
<212> TYPE: DNA
<213> ORGANISM: Artificial Sequence
<220> FEATURE:
<223> OTHER INFORMATION: 18s rRNA gene

<400> SEQUENCE: 19
actggtagct agcctggatc gatcgggtgt agtactga 38

<210> SEQ ID NO 20
<211> LENGTH: 16
<212> TYPE: DNA
<213> ORGANISM: Artificial Sequence
<220> FEATURE:
<223> OTHER INFORMATION: 18s rRNA gene

<400> SEQUENCE: 20
tagcctggat ccatcg 16

<210> SEQ ID NO 21
<211> LENGTH: 9
<212> TYPE: DNA
<213> ORGANISM: Artificial Sequence
<220> FEATURE:
<223> OTHER INFORMATION: 18s rRNA gene

<400> SEQUENCE: 21 tattactga 9

<210> SEQ ID NO 22
<211> LENGTH: 15
<212> TYPE: DNA
<213> ORGANISM: Artificial Sequence
<220> FEATURE:
<223> OTHER INFORMATION: 18s rRNA gene

<400> SEQUENCE: 22
taggtagcct ggatc 15

<210> SEQ ID NO 23
<211> LENGTH: 27
<212> TYPE: DNA
<213> ORGANISM: Artificial Sequence
<220> FEATURE:
<223> OTHER INFORMATION: 18s rRNA gene

<400> SEQUENCE: 23
tatcaacatc cttcctatta tatttct 27

<210> SEQ ID NO 24
<211> LENGTH: 26
<212> TYPE: DNA
<213> ORGANISM: Artificial Sequence
<220> FEATURE:
<223> OTHER INFORMATION: 18s rRNA gene

<400> SEQUENCE: 24
tatcaacatc cttcctatta tattct 26

<210> SEQ ID NO 25
<211> LENGTH: 28
<212> TYPE: DNA

-continued

```
<213> ORGANISM: Artificial Sequence
<220> FEATURE:
<223> OTHER INFORMATION: 18s rRNA gene

<400> SEQUENCE: 25

tatcaacatt ccttcctatt atatttct                                   28


<210> SEQ ID NO 26
<211> LENGTH: 27
<212> TYPE: DNA
<213> ORGANISM: Artificial Sequence
<220> FEATURE:
<223> OTHER INFORMATION: 18s rRNA gene

<400> SEQUENCE: 26

tatcgacatc cttcctatta tatatct                                    27
```